(12) United States Patent
Ziaie et al.

(10) Patent No.: US 10,300,259 B2
(45) Date of Patent: May 28, 2019

(54) SMART CAPSULE WITH GI-TRACT-LOCATION-SPECIFIC PAYLOAD RELEASE

(71) Applicant: Purdue Research Foundation, West Lafayette, IN (US)

(72) Inventors: Babak Ziaie, West Lafayette, IN (US); Rahim Rahimi, Lafayette, IN (US); Wuyang Yu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 542 days.

(21) Appl. No.: 14/919,120

(22) Filed: Oct. 21, 2015

(65) Prior Publication Data

US 2016/0114142 A1 Apr. 28, 2016

Related U.S. Application Data

(60) Provisional application No. 62/067,321, filed on Oct. 22, 2014.

(51) Int. Cl.
*A61M 31/00* (2006.01)
*A61B 5/07* (2006.01)
*A61B 5/00* (2006.01)

(52) U.S. Cl.
CPC ........... *A61M 31/002* (2013.01); *A61B 5/073* (2013.01); *A61B 5/4839* (2013.01); *A61B 5/42* (2013.01)

(58) Field of Classification Search
CPC ......... A61B 5/073; A61B 5/42; A61B 5/4839; A61B 1/041; A61B 1/00016; A61B 1/00027; A61B 5/06; A61B 5/062; A61M 2205/04; A61M 2205/10; A61M 2205/33; A61M 2205/36; A61M 31/00; A61M 31/002
USPC ......................................................... 604/514
See application file for complete search history.

(56) References Cited

U.S. PATENT DOCUMENTS

| 3,659,600 | A | 5/1972 | Merrill |
| 4,507,115 | A | 3/1985 | Kambara et al. |
| 5,217,449 | A | 6/1993 | Yuda et al. |
| 8,602,977 | B2 | 12/2013 | Fujimori et al. |
| 2003/0181788 | A1* | 9/2003 | Yokoi ............... A61B 1/00087 600/160 |
| 2005/0049488 | A1 | 3/2005 | Homan |
| 2008/0183041 | A1* | 7/2008 | Fujimori ........... A61B 1/00036 600/118 |

* cited by examiner

*Primary Examiner* — Jason E Flick
(74) *Attorney, Agent, or Firm* — Purdue Research Foundation

(57) ABSTRACT

A remotely activatable capsule. The capsule includes a housing that can be swallowed by a subject, an electrical energy reservoir having a first terminal and a second terminal positioned in the housing, a remotely activatable switch positioned in the housing and configured to be remotely activated, and a function-specific mechanism positioned in the housing and electrically coupled to the remotely activatable switch and to the electrical energy reservoir and configured to perform a function when the remotely activatable switch is activated.

9 Claims, 7 Drawing Sheets

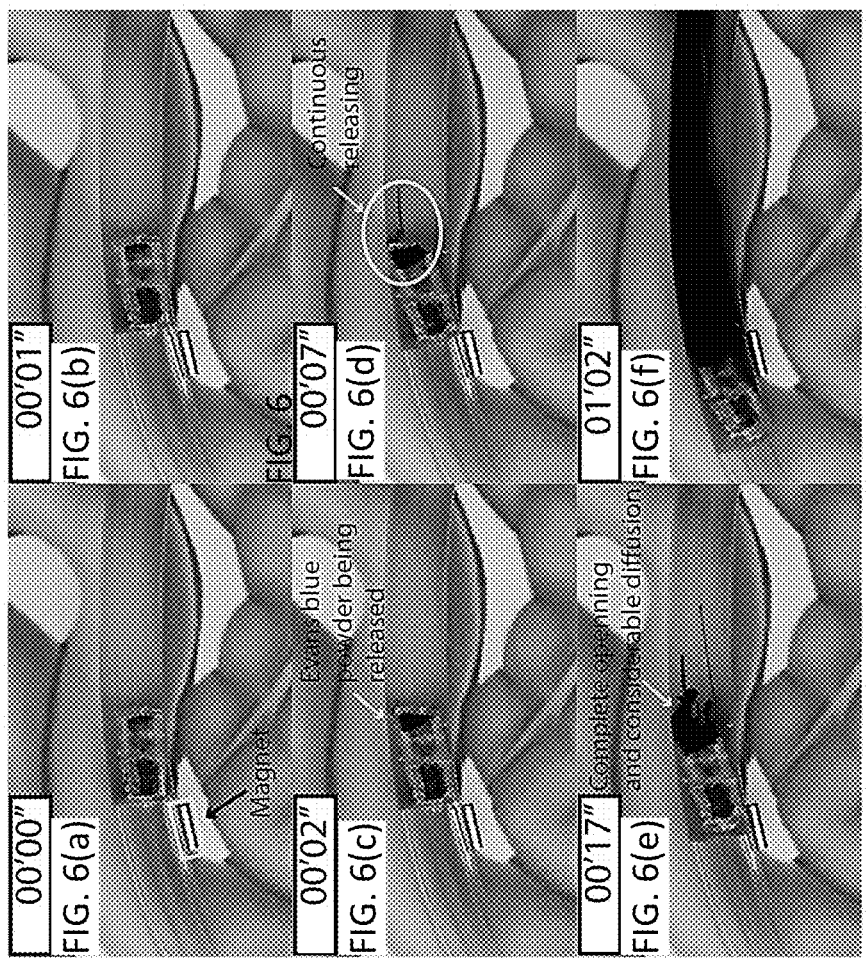

SMART CAPSULE WITH GI-TRACT-LOCATION-SPECIFIC PAYLOAD RELEASE

CROSS-REFERENCE TO RELATED APPLICATIONS

The present U.S. patent application is related to and claims the priority benefit of U.S. Provisional Patent Application Ser. No. 62/067,321, filed Oct. 22, 2014, the contents of which are hereby incorporated by reference in their entirety into the present disclosure.

TECHNICAL FIELD

The present application relates to drug delivery and in particular to an ingestible smart capsule capable of drug delivery at a selective location.

BACKGROUND

This section introduces aspects that may help facilitate a better understanding of the disclosure. Accordingly, these statements are to be read in this light and are not to be understood as admissions about what is or is not prior art.

In recent years smart capsules, which once ingested can perform endoscopy and biopsy, have been the focus of intense research and development. Included in this class of capsules is an endoscopic smart capsule used by gastroenterologists to collect images from hard-to-reach areas in the gastrointestinal (GI) tract (in particular the small intestine which cannot be reached via standard endoscopic methods, including colonoscopy). Pharmaceutical companies have also been interested in similar technologies for releasing medications at specific sites in the GI tract. Site-specific delivery can optimize the therapeutic efficacy of many drugs with preferential absorption sites. Exemplary capsules in the prior art are used in the pharmaceutical industry for studying human drug absorption. This capsule incorporates a spring-loaded cylinder which, once actuated and released by an RF signal, pushes a piston and forces the drug formulation out through a small hole. The location of the capsule is monitored through gamma ray scintillation imaging by incorporating a small amount of radioactive material in capsule. Other similar efforts in this area include a radiofrequency activated capsule relying on a shape-memory alloy actuator to rotate a cylinder and align a series of holes, allowing the drug to be released from a reservoir (location tracking was accomplished by x-ray fluoroscopy). Still other efforts include systems based on electrolytic actuation (gas production) or solid fuel micro-thrusters with the former being too slow for most practical applications and the latter posing safety issues related to high temperatures and pressures generated within the device.

Magnetically actuated capsules have also been investigated wherein a capsule which contracts or collapses under magnetic attraction to realize a multimodal drug release. In addition, a similar capsule made up of magnetic semi-hard and soft materials which disintegrates upon a demagnetization process is also known.

Although suitable for drug absorption studies in clinical-settings, the abovementioned approaches cannot be used for actual therapy in larger populations that can benefit from smart capsules which release the drug at an optimum location in the GI tract. This is mainly due to the problems associated with the need for real-time tracking of the capsule location (using either gamma rays or fluoroscopy both of which are not practical in a non-clinical setting and pose health hazards if used repeatedly). In addition, all these systems require active participation by the patient/volunteer or investigator in the form of triggering an RF transmitter once the capsule is in the targeted position. Such requirement is very difficult to enforce and/or guarantee (the capsule might reach the desired location in the middle of the night or at a time untimely for the required triggering).

There is, therefore an unmet need for a novel smart capsule capable of drug delivery to a selective location in the GI tract without the need for monitoring of the capsule's location in the tract.

SUMMARY

A remotely activatable capsule is disclosed. The capsule includes a housing that can be swallowed by a subject. The capsule also includes an electrical energy reservoir having a first terminal and a second terminal positioned in the housing. The capsule also includes a remotely activatable switch positioned in the housing and configured to be remotely activated. The capsule further includes a function-specific mechanism positioned in the housing and electrically coupled to the remotely activatable switch and to the electrical energy reservoir and configured to perform a function when the remotely activatable switch is activated.

A method for remotely releasing a drug in a subject is also disclosed. The method includes providing a therapeutically effective dosage of a drug in a magnetically activatable capsule. The method further includes administering the remotely activatable capsule to the subject. The method further includes placing a magnetic field about the remotely activatable capsule at a selective position corresponding to a physiologically desirable position such that the remotely activatable capsule releases the therapeutically effective dosage of the drug at the physiologically desirable position. The magnetic field can be provided by an implanted magnet or by an externally worn magnet.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIGS. 6(a)-6(f) depict schematic views of the progress of the smart capsule according to the present disclosure as it passes through a simulated gastrointestinal (GI) tract.

FIG. 8 depicts a graph of capacitance measured in μF and voltage measured in V for the capacitance of FIG. 1 to cause burning of the fuse of FIG. 1.

FIG. 9 depicts a block diagram of a remotely activatable device, according to the present disclosure.

Figure 1:
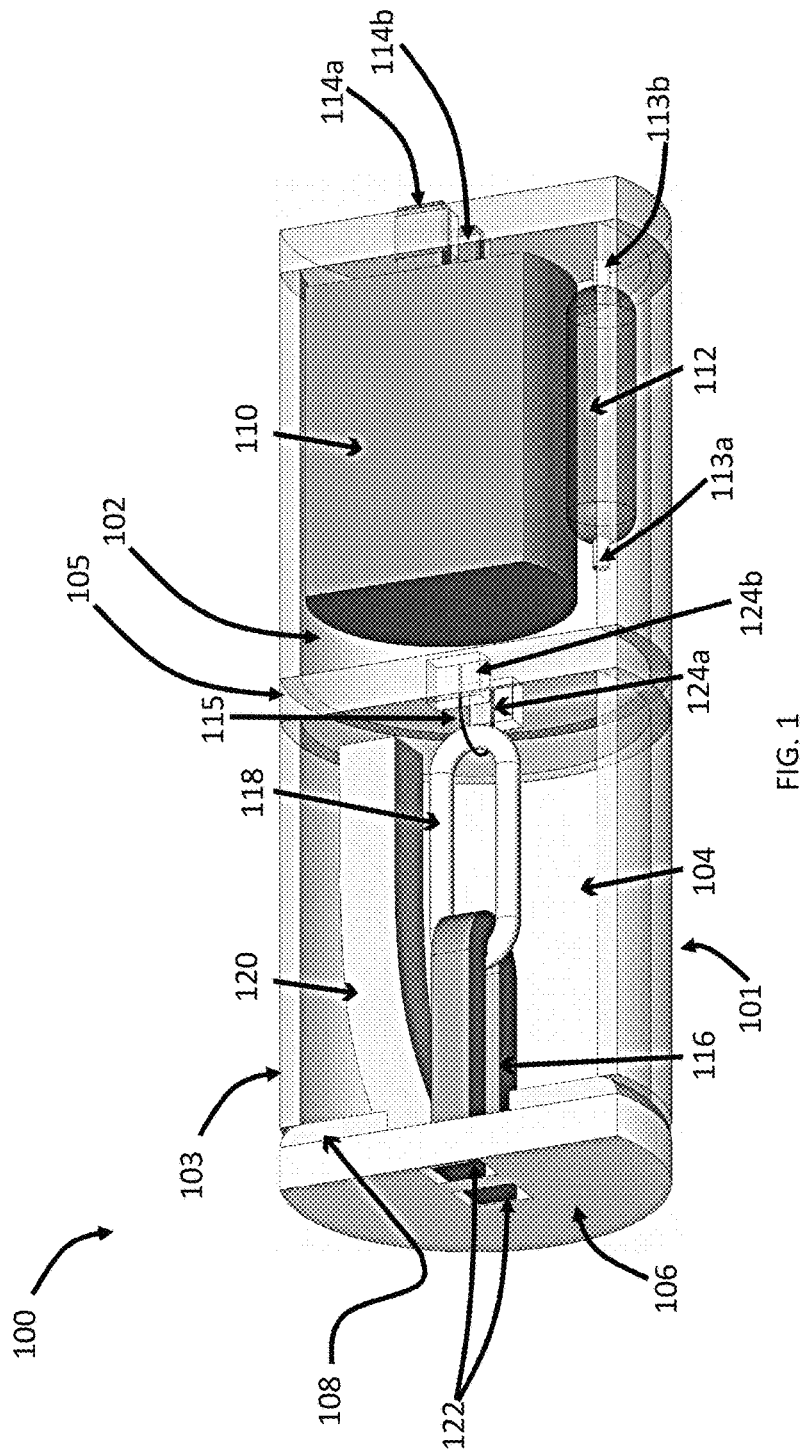
FIG. 1 depicts a perspective cutout view of a smart capsule including a magnetic switch, a heating element, a fuse, and two counteracting biasing members, according to the present disclosure.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel smart capsule capable of drug delivery to a selective location in the GI tract without the need for monitoring of the capsule's location in the tract is disclosed. According to the present disclosure, a remotely activatable capsule 100, depicted in FIG. 1 where a cutout perspective view is depicted, which includes a hosing 101. The housing 101 is divided into two compartments: an electrical component compartment 102 and a drug compartment 104. The two compartments are separated by a separator 105. These two compartments are encased by a main body 103 and a detachable cap 106. The detachable cap 106 is sealably coupled to the main body 103 by a sealing member 108.

In the electrical compartment 102, there is an electrical energy reservoir 110 and a magnetic switch 112. The magnetic switch 112 also has two terminals 113a and 113b. The electrical energy reservoir 110 also has two terminals 114a and 114b, optionally disposed at the outside surface of the housing 101. The terminals 114a and 114b can be used to pre-charge the electrical energy reservoir 110. The electrical energy storage reservoir 110 can be a capacitor or a battery, however, a capacitor is typically smaller in size. One of the terminals 113a and 113b of the magnetic switch 112 is coupled to one of the terminals 114a and 114b of the electrical energy reservoir 110, while the other terminal is coupled to a heating wire 115 disposed in the drug compartment 104 at one of two terminals 124a or 124b. The other terminal 124b or 124a of the heating wire 115 is coupled to the other terminal 114a or 114b of the electrical energy reservoir 110.

Within the drug compartment 104, a fuse member 118 is coupled to the heating wire 115 such that in an activation mode when the heating wire 115 becomes hot, the fuse member 118 burns and decouples from the heating wire 115. An exemplary heating wire can be a length of nichrome wire. A biasing member 116 is coupled to the fuse member 118 at one end and to the detachable cap 106 at the other end via fasteners 122 such that when the fuse member 118 is in the intact state (i.e., in the inactivation mode), the biasing member 116 pulls the detachable cap 106 sealably against the main body 103 via the sealing member 108; and when in the burnt state (activation mode), provides no biasing force against the detachable cap 106. An exemplary fuse member can be a nylon fuse with a melting point of about 60-85° C. The sealing member 108 can be made from Polydimethylsiloxane (PDMS).

Also shown in FIG. 1 is a biasing member 120 in the drug compartment 104 which biases the detachable cap 106 outward. The biasing member 120 is shown as a mechanical spring member positioned between the separator 105 and the interior surface of the detachable cap 106. It should be appreciated that the biasing member 120 exerts an outwardly biasing force on the detachable cap 106 that is smaller than the inwardly biasing force exerted by the biasing member 116. Therefore, in the intact state (inactivation mode) the detachable cap 106 is sealably secured against the main body 103 by the sealing member 108. It should also be noted that while a mechanical biasing member 120 is depicted in the drug compartment 104, the outwardly biasing force can also be provided by means other than a mechanical biasing member. For example, the biasing force can be generated via fluid pressure (not shown) acting on the detachable cap 106. The fluid can be air or gasified saline. In these embodiments, the outwardly biasing force exerted on the detachable cap 106 remains less in the intact state (inactivation mode) than the inwardly biasing force exerted on the detachable cap 106 by the biasing member 116. In another embodiment, gas can be generated via electrolysis. For example a specific volume of a water based fluid can be placed in the drug compartment 104 such that it comes in contact with electrolysis electrodes (not shown) that are coupled to the electrical energy reservoir 110. The charge in the electrical energy reservoir 110 can cause separation of the water in the water-based fluid into oxygen and hydrogen within the drug compartment 104. The volume of the fluid may be such that it generates an appropriate amount of pressure within the drug compartment. Alternatively, the magnetic switch 112 may be configured to provide a two stage activation. In the first stage, the magnetic switch 112 couples the electrical energy reservoir 110 to the electrolysis electrodes (not shown) designed to generate gas pressure. In the second and delayed stage, the magnetic switch 112 coupled the electrical energy reservoir 110 to the heating wire 115 in order to cause release of drug.

The biasing member 116 can be made from an elastic material or a spring-like arrangement as is known to a person having ordinary skill in the art. Similarly, the biasing member 120 can be made from a spring-like material suitable for providing an outwardly biasing force on the detachable cap 106.

While not shown, the drug compartment 104 is configured to be filled with a drug compound that can be released when the remotely activatable capsule 100 is placed in the activation mode (i.e., when the magnetic switch 112 comes in close proximity to a magnetic force causing the magnetic switch 112 to be closed, releasing the electrical energy held in the electrical energy reservoir 110 to the heating wire 115, causing burning of the fuse member 118, thereby ceasing the inwardly exerted force on the detachable cap 106, which then is detached from the main body 103 due to the outwardly exerted biasing force exerted by the biasing member 120 thereby releasing the drug in the drug compartment).

Figure 2:
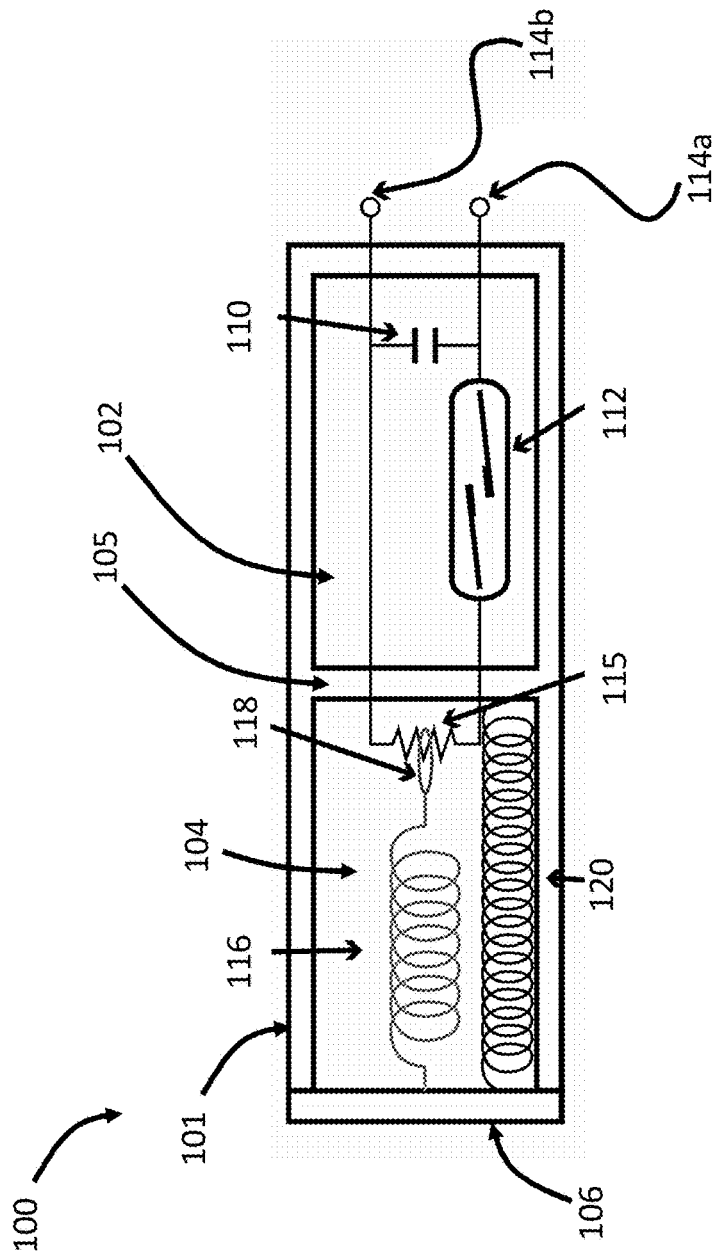
FIG. 2 depicts an electromechanical lumped parameter schematic view of the smart capsule of FIG. 1.
Figure 3:
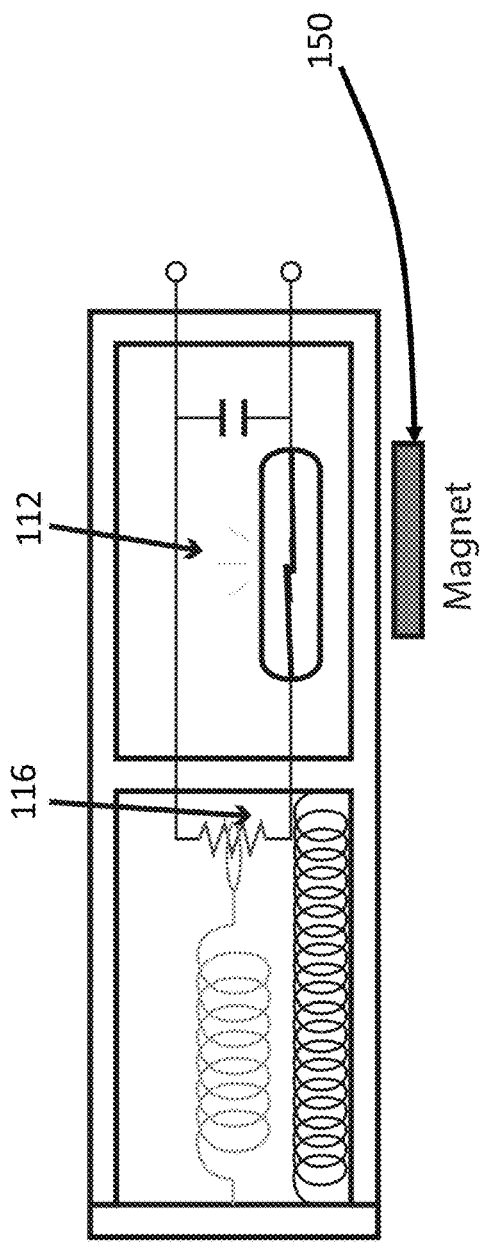
FIG. 3 depicts the schematic of FIG. 2 when the smart capsule has come in proximity to a magnetic force with sufficient effect to cause the magnetic switch to close.
Figure 4:
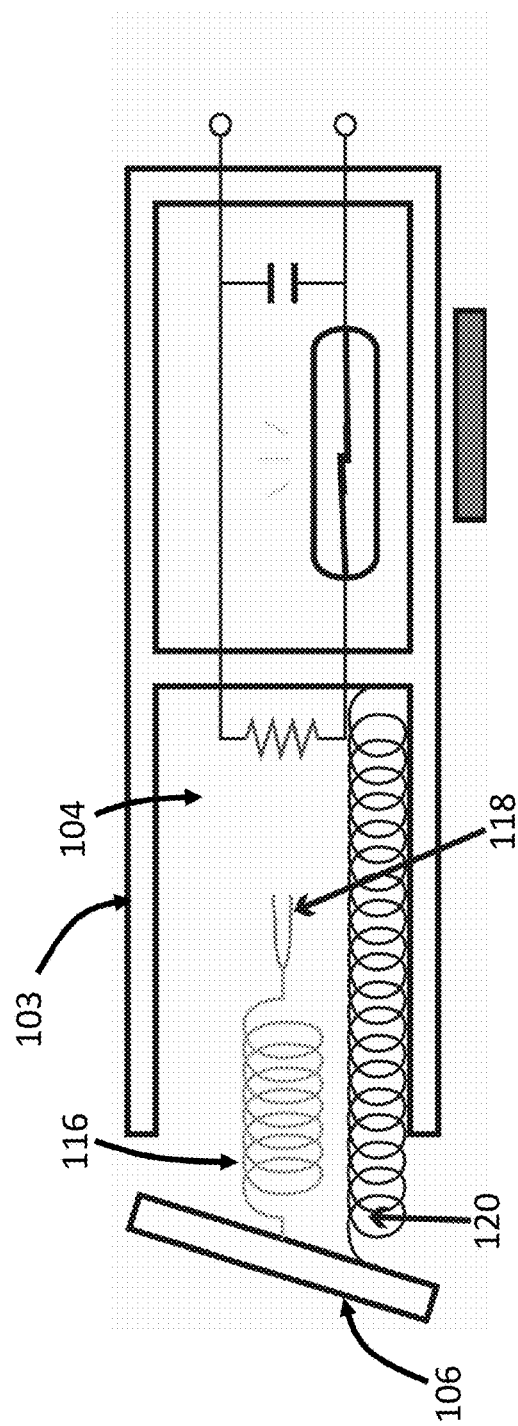
FIG. 4 depicts the schematic of FIG. 3, when the fuse has burnt activating the two counteracting biasing members.

Referring to FIGS. 2, 3, and 4, the operational aspect of the remotely activatable capsule 100 is depicted in schematic form. In FIG. 2, the magnetic switch 112 is depicted as being electrically coupled on one end to the terminal 114a also coupled to the electrical energy reservoir 110 and on the other end to the heating wire 115 which in turn is coupled to the terminal 114b and the electrical energy reservoir 110. The magnetic switch is shown in an open position (inactivation mode) thus providing an open circuit between the electrical energy reservoir 110 and the heating wire 115. As described above, the inwardly biasing force exerted on the detachable cap 106 by the biasing member 116 is greater than the outwardly exerted biasing force exerted by the biasing member 120).

Referring to FIG. 3, when a magnetic force is brought to the magnetic switch, e.g., by bringing the remotely activatable capsule 100 in close proximity to a magnet 150, the magnetic switch 112 closes thereby placing the remotely activatable capsule 100 in the activation mode. Referring to FIG. 4, the fuse member 118 has burnt and separated from the heating wire, thereby ceasing the outwardly biasing force exerted by the biasing member 116, causing the detachable cap 106 to be separated from the main body 103 by the outwardly biasing force of the biasing member 120, thereby allowing the drug held in the drug compartment 104 to be delivered to a location selectively selected by positioning the magnetic force.

Figure 5:
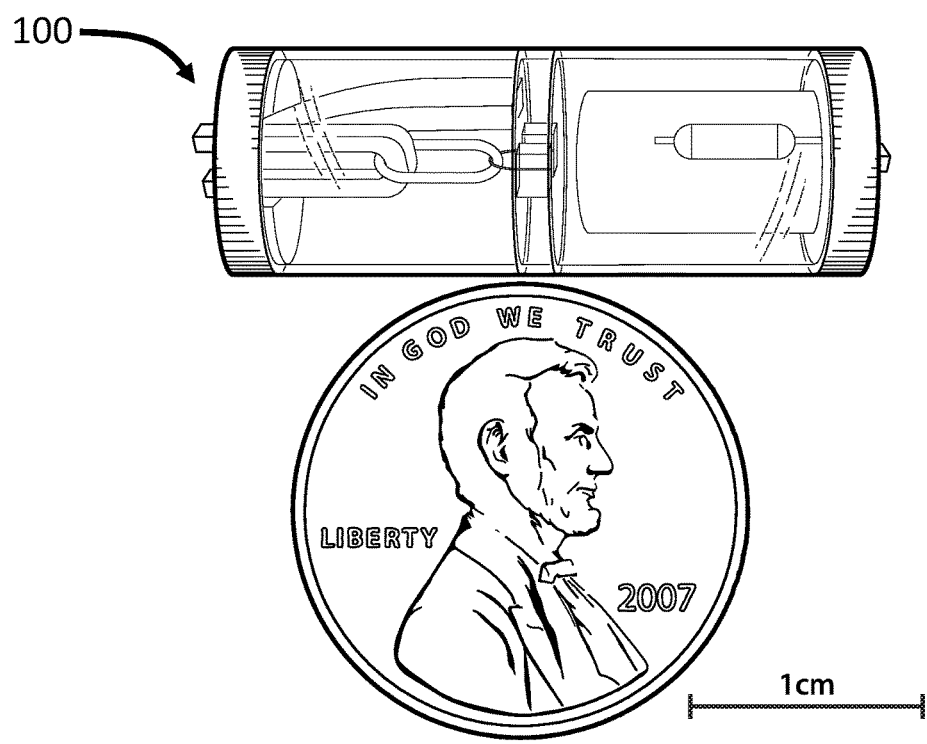
FIG. 5 depicts a relative size of the smart capsule according to the present disclosure as compared to a U.S. penny.

Referring to FIG. 5, the relative size of the remotely activatable capsule 100 according to one embodiment is depicted. The size is compared to a U.S. penny to illustrate its size.

Referring to FIGS. 6(*a*)-6(*f*) progress through a simulated GI tract is depicted as the remotely activatable capsule 100 travels through the tract. The magnet depicted in the tract is implanted at a location where the remotely activatable capsule 100 is intended to release its drug payload in order to provide an internal magnetic force. Alternatively, the magnet can be placed externally, e.g., on a belt, outside the subject's body in order to provide an external magnetic force. FIG. 6(*b*) depicts the movement of the remotely activatable capsule 100 at 1 second. At 2 seconds (FIG. 6(*c*)) the remotely activatable capsule 100 is placed in sufficient proximity to the magnet such that the remotely activatable capsule 100 activates thereby beginning to release a dye to indicate drug release. As the remotely activatable capsule 100 travels down the tract at 7 seconds, 17 seconds, and at 1 minute 2 seconds, the dye continue to be expelled from the remotely activatable capsule 100 simulating release of a drug.

Considering the GI tract anatomy and as a matter of practical application, the described remotely activatable capsule is suited according to one embodiment for drug release at the junction of small and large intestine (ileocecal valve). This location is relatively constant among individuals (lower right quadrant, over the appendix) and an externally worn magnet on the belt can trigger the release, thus making the device useful for treating large intestine diseases such as Crohn disease, inflammatory bowel disease, *c. difficile* infection, and colon cancer.

The housing 103 can be made from acrylic using a laser machining system. The following procedure is to be considered as an exemplary process and no further limitation is intended thereby.

First, four annuli (9 mm outer diameter and 8.4 mm inner diameter), were cut from a 5.58 mm thick acrylic sheet. These were stacked and glued together to form the lateral wall of the capsule. Next, three discs (9 mm diameter×1 mm height) were cut to form the end caps and the dividing wall. Two 1.45 mm×0.60 mm windows were opened on the separating wall and the end cap for exposing the nichrome wire and the charging pins respectively. Other two 1.65 mm×1.15 mm windows were opened on the release cap for guiding the rubber bands. We should emphasize that one can fabricate the casing using other materials and machining methods as long as the material is biocompatible, low cost, non-magnetic (to allow the actuation), and easily machinable.

A magnetic switch and a capacitor (e.g., a 1 F, 2.7 V, 10.5 mm×6.3 mm) were electrically connected via a soldered copper wire. Two more (copper) leads were separately soldered onto the capacitor and the magnetic switch. Next, the switch and the capacitor were placed into the capsule and the end cap was affixed. Glue was used for joining acrylic parts. The dividing wall was then glued onto the opposite opening to encapsulate the switch and the capacitor while allowing the suspended copper wires out through the two windows in the cap (also referred herein as the detachable cap). A 2-3 mm segment of nichrome wire (Nichrome 60, 70.2 ohms/foot, Dia. 0.0031 inches) was soldered to the copper wires, and the window was sealed. A length of fusible nylon thread was passed through the loop shaped by the nichrome wire, and its two ends were joined by heat melting to form a ring. A strip of rubber band (1×1 mm² cross section) was trimmed by a blade and intertwined through the thread ring. Next, the drug was loaded, and the casing of the drug reservoir was glued to the capacitor and magnetic switch compartment. Before final closure, a flexible PDMS rod slightly longer than the height of the chamber, acting as a pre-loaded spring, was placed inside to ensure its opening following the magnetic actuation. We should emphasize that the remotely activatable capsule concept presented here can be made smaller than a standard 000 size gelatin capsule (i.e., 9.97 mm×26.14 mm). Table I provides a summary of the capsule specifications.

TABLE I

SPECIFICATIONS OF THE PROTOTYPE CAPSULE

| Capsule enclosure | | | |
|---|---|---|---|
| Outer diameter | 9 mm | | |
| Length | 26 mm | | |
| Inner diameter | 8.4 mm | | |
| Separating wall and caps' thickness | ~1 mm | | |
| Drug reservoir volume | 0.618 mL | | |
| Reed switch | | | |
| Profile dimension | 1.8 mm (MAX) | Switching voltage | <100 V |
| Tube length | 7 mm | Switching current | <1A |
| Capacitor | | | |
| Diameter | 6.3 mm | Capacitance | 1 F |
| Height | 10.5 mm | Rated voltage | 2.7 V |
| Nichrome wire | | | |
| Resistance/unit, length | 2.3 Ω/cm | | |
| Length | 2~3 mm | | |
| Fusible nylon thread | | | |
| Melting point | 60~85° C. | | |
| PDMS rod | | | |
| Height | 12.5 mm | | |
| Profile dimension | 1.2 mm × 1.2 mm | | |

To characterize the magnetic switch, the switch response to amplitude and orientation of the field has was determined. For these experiments, a small permanent cylinder magnet (3 mm in diameter and 12.7 mm in height with a surface magnetic field of 7343 Gauss) was positioned at various distances and orientations with respect to the magnetic switch.

Figures 7A, 7B:
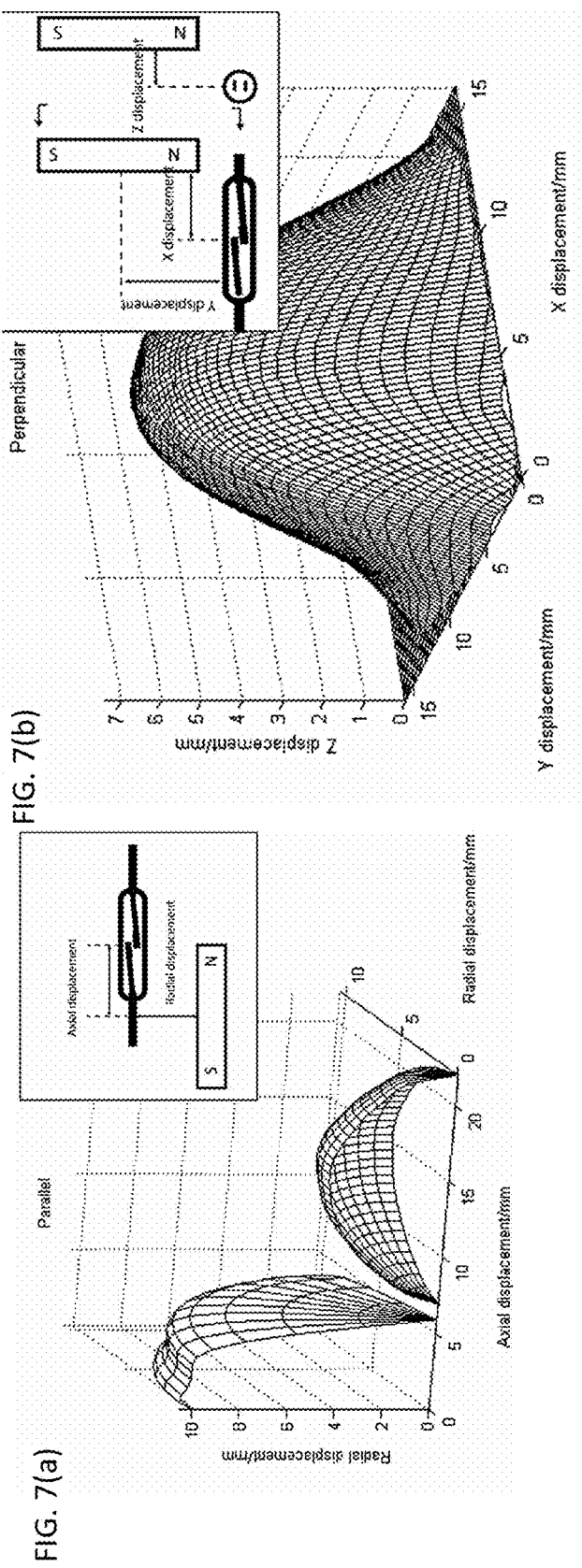
FIG. 7(a) depicts a graphical representations of radial displacement vs. axial displacement for a parallel interface between the magnetic switch of FIG. 1 and a magnet generating the magnetic force of FIG. 3.
FIG. 7(b) depicts a graphical representations of radial displacement vs. axial displacement for a perpendicular interface between the magnetic switch of FIG. 1 and a magnet generating the magnetic force of FIG. 3.

FIGS. 7(a) and 7(b) show maps of the spatial regions around the magnetic switch which allows magnetic actuation with the small permanent magnet. When a switch and magnet move such that their longitudinal axes are parallel with respect to each other, FIG. 7(a), the region of actuation is radially symmetrical. In this case, the magnetic switch will be triggered if the magnet lies within the envelope, an eighth of which is shown in FIG. 7(a). The data reveals that actuation can occur at distances of up to 11 mm above the center of the longitudinal axis of the cylindrical magnet (central envelop in FIG. 7(a)). This value is sufficient to trigger the magnetic switch in the intestine model used herein, since the capsule is expected to drift by the magnet at a distance of no more than 13 mm based on the anatomical dimensions, the capsule casing thickness and the magnetic switch diameter. Magnets with stronger field, hence wider actuation range, might be required for in-vivo implantation to completely cover the diameter of the small intestine (about 2.5 cm); alternatively, one can implant two smaller ones each at one side of the small intestine to ensure proper actuation (other configuration such as staggering can also be used). The off-center envelope in FIG. 7(a) indicates a maximum switching distance of 5 mm when the capsule approaches the magnet from either side.

In another scenario, where the magnetic switch and magnet move such that their longitudinal axes are orthogonal to each other, the actuation occurs within four spherical regions around the magnet, an octant of which is illustrated in FIG. 7(b). However, as the graph shows, this configuration makes the actuation more difficult, in particular near the midpoint (due to the orthogonality of the magnetic field and the magnetic switch axis). Since it is more probable that the capsule transits in the bowel with its long axis along the length of the intestine, the parallel orientation of the magnet relative to the magnetic switch (case shown in FIG. 7(b)) is a more realistic configuration.

With the nichrome wire resistance fixed, an appropriate capacitor that satisfies requirement for burning out the fuse member. From a stored energy perspective ($0.5\ CU^2$), a larger capacitance reduces the required charging voltage for a given total energy. A high charging voltage can cause several difficulties such as peak discharge current beyond the limit of the magnetic switch (thus destroying the switch). However, a large capacitor usually means increased dimensions of the capsule and a higher equivalent series resistance (ESR). FIG. 8 shows the results of experiments done using a fixed value for the nichrome wire (2 mm long, 0.08 mm thick, resulting in about 0.23 ohms) in order to determine the capacitance and charging voltage required to heat the wire high enough to melt the nylon fuse. As can be seen, a super capacitor of 1 F used in our capsule requires a charging voltage of 1 volt for proper operation, whereas, a 100 µF capacitor has to be charged to 16 volts.

While a remotely activatable capsule is described herein, it should be appreciated that the scope of the present disclosure covers an ingestible device that can be remotely activated to thereby release electrical energy from an electrical energy reservoir (e.g., a capacitor, a battery, etc.) to perform a specific function. The remote activation can be accomplished by a proximity switch. An example of such a proximity switch is described herein as a magnetic switch that is activatable by proximity to a magnetic field. However, other types of proximity switches are possible. Other examples may include a PH-based sensor/switch where the switch activates when the localized PH reaches a certain level at which point the switch activates releasing the electrical energy in the reservoir.

Insofar as the function that remotely activatable device can perform, it should be appreciated that many other functions besides releasing a drug are within the scope of the present disclosure. Referring to FIG. 9, a block diagram of a remotely activatable device 200, according to the present disclosure is depicted. The remotely activatable device 200 includes an electrical energy storage reservoir 202, a remotely activatable switch 204, and a function-specific mechanism 206. The remotely activatable switch 204 can be a proximity switch as described above.

The function-specific mechanism 206 is described below in various embodiments. First, the function-specific mechanism 206 is a drug delivery mechanism as described herein. Alternatively, the function-specific mechanism 206 includes activation of a camera with a light source at a selective location such that the remotely activatable device 200 begins to capture images only when it has reached a specific location in the GI tract. This embodiment provides a significant advantage over prior art ingestible pill cameras where the camera only captures images once it has reached a specific location.

In another embodiment, the function-specific mechanism 206 is a light source. Once triggered, the function-specific mechanism 206 activates a light source which can then activate a light-activated rug in the GI tract. In yet another embodiment, the function-specific mechanism 206 generates ultrasound. Once triggered, the function-specific mechanism 206 generate ultrasound that can be used to image the GI tract.

In yet another embodiment, in addition to the main function performed by the function-specific mechanism 206, the function-specific mechanism 206 also generates a radiofrequency (RF) signal that can be used to signal performance of the function. For example, if the function-specific mechanism 206 is to deliver a drug, at some time after activation, it can generate an RF signal indicating the drug has been delivered.

Those skilled in the art will recognize that numerous modifications can be made to the specific implementations described above. The implementations should not be limited to the particular limitations described. Other implementations may be possible.

The invention claimed is:
1. A remotely activatable capsule, comprising:
   a housing configured to be swallowed by a subject, the hosing comprising a main body and a detachable cap positioned at one end of the main body;
   an electrical energy reservoir having a first terminal and a second terminal disposed in the housing;
   a remotely activatable switch disposed in the housing and configured to be remotely activated, the remotely activatable switch is a magnetic switch having a first terminal and a second terminal, the first terminal of the magnetic switch coupled to the first terminal of the electrical energy reservoir, the magnetic switch configured to be i) open in a non-activation mode thereby providing an open circuit between the first and second terminals of the magnetic switch, and ii) closed in an activation mode when a magnetic field is applied thereby providing a closed circuit between the first and second terminals of the magnetic switch, wherein the magnetic field can be provided by an implanted magnet or by an externally worn magnet;
   a drug compartment containing a drug, the drug compartment disposed in the housing and electrically coupled to the remotely activatable switch and to the electrical energy reservoir and configured to release the drug when the remotely activatable switch is activated, the drug compartment comprising a release mechanism electrically coupled to the second terminal of the magnetic switch and to the second terminal of the electrical energy reservoir and mechanically coupled to the detachable cap, the release mechanism configured to i) sealably maintain the detachable cap against the main body of the housing in the non-activation mode, and ii) allow the cap to be detached from the main body in the activation mode, the release mechanism comprising:

a first biasing member coupled to the detachable cap and held in a biased position in the non-activation mode;

a heating wire coupled to the second terminal of the magnetic switch and to the second terminal of the electrical energy reservoir; and a fuse member disposed between the heating wire and the first biasing member and configured to burn in the activation mode and thereby cause the first biasing member to move from the biased position to an unbiased position.

2. The remotely activatable capsule of claim 1, the release mechanism further comprising a space filled with a fluid under pressure, wherein in the activation mode, the fluid pressure causes the detachable cap to become detached, and wherein the biasing force exerted by the first biasing member is greater than the force acting on the detachable cap by the fluid pressure.

3. The remotely activatable capsule of claim 2, wherein the fluid is air.

4. The remotely activatable capsule of claim 2, wherein the fluid is gasified saline.

5. The remotely activatable capsule of claim 1, the release mechanism further comprising a second biasing member coupled to the detachable cap and to the main body and bias to detach the detachable cap, wherein the biasing force of the first biasing member is greater than then biasing member of the second biasing member.

6. The remotely activatable capsule of claim 1, the electrical energy reservoir is a capacitor.

7. The remotely activatable capsule of claim 1, the housing includes two terminals coupled to the capacitor for charging the capacitor.

8. The remotely activatable capsule of claim 1, the electrical energy reservoir is a battery.

9. The remotely activatable capsule of claim 1, the housing is made from a polymer-based material.

* * * * *